US007914791B1

(12) United States Patent
Hirst et al.

(10) Patent No.: US 7,914,791 B1
(45) Date of Patent: Mar. 29, 2011

(54) VACCINE

(75) Inventors: Timothy Raymond Hirst, Taunton (GB); Neil Andrew Williams, Cross (GB); Andrew Morgan, Henleaze (GB); Andrew Douglas Wilson, Winscombe (GB); Lucy Amber Bird, Chichester (GB)

(73) Assignee: Trident Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 09/674,935

(22) PCT Filed: May 10, 1999

(86) PCT No.: PCT/GB99/01461
§ 371 (c)(1),
(2), (4) Date: Dec. 21, 2000

(87) PCT Pub. No.: WO99/58145
PCT Pub. Date: Nov. 18, 1999

(30) Foreign Application Priority Data

| May 8, 1998 | (GB) | ................................... | 9809958.3 |
| Jun. 3, 1998 | (GB) | ................................... | 9811954.8 |
| Jun. 8, 1998 | (GB) | ................................... | 9812316.9 |

(51) Int. Cl.
*A61K 39/00* (2006.01)
*A61K 39/38* (2006.01)
*A61K 39/40* (2006.01)
*A61K 45/00* (2006.01)
*A61K 51/00* (2006.01)

(52) U.S. Cl. .................. 424/184.1; 424/1.41; 424/85.2; 424/85.4; 424/150.1; 424/154.1; 424/159.1; 424/161.1; 424/164.1; 424/189.1; 424/196.11; 424/197.11; 424/201.1; 424/231.1; 424/236.1; 424/241.1; 424/278.1; 435/7.24; 435/334; 530/388.23; 530/388.4; 530/389.6

(58) Field of Classification Search ............... 424/236.1, 424/206.1, 189.1, 248.1, 272.1, 1.11, 130.1, 424/147.1, 159.1, 178.1, 184.1, 230.1, 231.1, 424/278.1, 281.1
See application file for complete search history.

(56) References Cited

U.S. PATENT DOCUMENTS

| 5,182,109 A | 1/1993 | Tamura et al. |
| 5,241,053 A | 8/1993 | Fujisawa et al. |
| 5,681,571 A * | 10/1997 | Holmgren et al. ......... 424/236.1 |
| 6,019,973 A | 2/2000 | Holmgren et al. |
| 6,103,243 A | 8/2000 | Russell-Jones et al. |

(Continued)

FOREIGN PATENT DOCUMENTS

AU 2003261492 A1 12/2003

(Continued)

OTHER PUBLICATIONS

Marcello et al. (Proc. Natl. Acad. Sci. USA, vol. 91, pp. 8994-8998, Sep. 1994).*

(Continued)

*Primary Examiner* — Mark Navarro
*Assistant Examiner* — JaNa Hines
(74) *Attorney, Agent, or Firm* — Mintz, Levin, Cohn, Ferris, Glovsky and Popeo, P.C.

(57) ABSTRACT

A method for stimulating the immune response to a vaccine applied to a mammalian subject includes the step of administering to the subject an effective amount of EtxB or a molecule having substantially equivalent activity, free from whole toxin and not linked to an antigen.

7 Claims, 15 Drawing Sheets

Level of Ig or IgA in MS or IgA in EW compared with control mice following immunisation with HSV-1 or mock Gp preparations with different amounts of rEtxB

U.S. PATENT DOCUMENTS 6,413,523 B1 * 7/2002 Clements ............... 424/241.1

FOREIGN PATENT DOCUMENTS

| | | | |
|---|---|---|---|
| AU | 2003261492 B2 | | 9/2006 |
| AU | 2006249261 A1 | | 1/2007 |
| CA | 2331832 A1 | | 11/1999 |
| EP | 372928 | | 6/1989 |
| EP | 0372928 A2 | | 6/1990 |
| EP | 919243 | | 11/1997 |
| EP | 0 722 340 | | 4/1998 |
| EP | 0 222 835 | | 4/2000 |
| GB | 2 217 600 | | 11/1989 |
| NO | 20002613 A1 | | 8/2009 |
| WO | WO 96/34893 | | 11/1996 |
| WO | WO 97/02045 | * | 1/1997 |
| WO | WO 99/26654 | | 6/1999 |
| WO | WO 99/36088 | | 7/1999 |
| WO | 99/58145 A2 | | 11/1999 |
| WO | 99/58145 A3 | | 2/2000 |

OTHER PUBLICATIONS

Hazama et al. 1993. Immunology. vol. 78(4): 643-649.*
Cruse et al. 1995. Illustrated Dictionary of Immunology. CRC Press Inc. pp. 18-19, 33, 152 and 192.*
Richards et al., (1997. Vaccine. vol. 15(10): 1065-1069).*
Wu and Russel (1998), Vaccine. 16(2-3):286-92.
Norwegain Office Action, Application No. 2000 5599, Date: Jul. 2, 2009 (with English translation).
International Prelminary Examination Report, App. No. PCT/GB99/01461, Date: Jul. 10, 2000.
Examination Report, Application No. EP99922284.7, Date: Sep. 21, 2007.
Examination Report, Application No. EP99922284.7, Date: Aug. 31, 2004.
Examination Report, Application No. EP9992284.7, Date: Jul. 22, 2003.
Examination Report, Application No. AU2003261492, Date: Jun. 15, 2005.
Examination Report, Application No. AU39394/99, Date: Jul. 21, 2003.
Examination Report, Application No. AU39394/99, Date: Feb. 8, 2002.
Office Action, Application No. CA2331832, Date: Mar. 2, 2009.
Japanese Office Action, Application No. JP2000-547996, Mail Date: Jun. 4, 2009 (with English Translation).
Blanchard et al. (1998), Immunology, 94(1):22-27.
Matousek et al. (1996), Journal of Immunology, 156(11):4137-45.
Vadolas et al. (1995), Eur J Immunology, 25(4):969-75.
Hirst, T.R., et al., J. Applied Microbiology Symp. Supp. 84: 26S-34S (1998).
Nashar, T.O., et al., Immunology, 91: 572-578 (1997).
Nashar, T.O., et al., Med. Microbiol. Immunol. 187: 3-10 (1998).
Richards, C.M., et al., J. Infect. Dis. 177: 1451-1457 (1998).
Williams, N.A., et al., Immunology Today 20: 95-101 (1999).
Zhang, T., et al., Infect. & Immun. 63: 1349-1355 (1995).
Boirivant, M., et al., The Journal of Immunology, 2001, 166: 3522-3532.
Sobel, D.O., et al., Diabetes, 1998, 47: 186-191.
Tamura et al., "*Escherichia coli* heat-labile enterotoxin B subunits supplemented with a trace amount of the holotoxin as an adjuvant for nasal influenza vaccine", Vaccine (1994), 12(12):1083-1089.

* cited by examiner

FIGURE 1

Level of Ig or IgA in MS or IgA in EW compared with control mice following immunisation with HSV-1 or mock Gp preparations with different amounts of rEtxB

- A-HSV-1 Gp + 10µg rEtxB
- B-HSV-1 Gp + 20µg rEtxB
- C-Mock Gp + 20µg rEtxB
- neg T cell proliferation of MLN or CLN lymphocytes from mice given HSV-1 glycoproteins (gp) with 10μg (A), 20μg (B) rEtxB or mock Gp with 20μg rEtxB (C) by the i.n. route cultured *in vitro* with HSV-1, mock or no antigen

FIGURE 4

Anti-HSV-1 serum Ig in mice following administration of HSV-1 glycoproteins three times at 10 day intervals with variable amounts of rEtxB or rCTB as adjuvant Figure 5a. Incidence of virus shedding from the eye following corneal scarification of mice with HSV-1 (SC16)

| Day post infection | 10μg rEtxB + HSV-1 gp (%)[1] | 20μg rEtxB + HSV-1 gp (%) | 20μg rEtxB + mock gp[2] (%) |
| --- | --- | --- | --- |
| 1 | 0 | 30 | 60 |
| 2 | 60 | 80 | 95 |
| 3 | 60 | 80 | 95 |
| 6 | 10 | 0 | 70 |
| 7 | 10 | 0 | 70 |
| 8 | 0 | 0 | 10 |
| 9 | 0 | 0 | 0 |

[1] Percentage of animals from which wash fluid from the eye secretions revealed the presence of live viral particles in a plaque assay.

[2] Mock infected animals were given an inoculum of glycoproteins prepared from uninfected tissue culture cells.

Figure 5b. Clinical disease following corneal scarification of mice with HSV-1 (SC16)

| | Corneal ulcers[2] | Oedema | Lid disease | Zosteriform infection | Encephalitis | Latency[1] TG1 | TG2 | TG3 |
| --- | --- | --- | --- | --- | --- | --- | --- | --- |
| 10μg rEtxB + HSV-1 gp | 80% | 0% | 0% | 0% | 0% | 22% | 11% | 0% |
| 20μg rEtxB + HSV-1 gp | 70% | 0% | 0% | 0% | 0% | 80% | 10% | 0% |
| 20μg rEtxB + mock gp | 80% | 45% | 55% | 40% | 40% | 83% | 30% | 16% |

[1] Latency was determined by extraction of the trigeminal ganglion (TG) from surviving mice 2 months after infection and coculturing with Vero cells. Figures given are for each of the lobes of the TG (TG1, TG2 and TG3).

[2] Figures are percentage of animals showing signs of the described symptoms at any point during acute infection. Each mouse was examined on a daily basis during the first 11 days of infection.

N=15 per group

FIG. 6

Ig Isotype distribution in MS from mice following infection (pos) or immunisation with HSV-1 Gp in the presence of EtxB or CTB as adjuvant

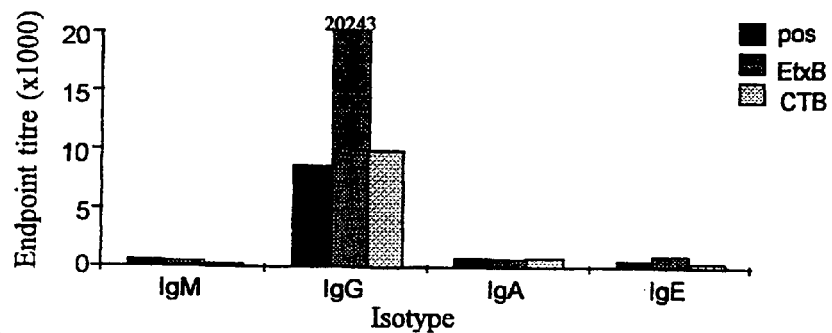

FIG. 7

Adjuvant effect of different amounts of rEtxB or rCtB on the level of HSV-1 specific IgA in eye washings following administration with HSV-1 glycoproteins

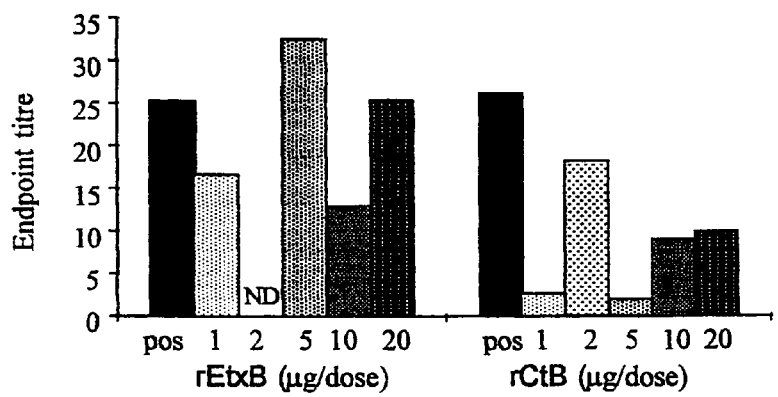

FIG 8. Distribution of subclasses following administration of HSV-1 Gp i.n. with either rEtxB or rCTB as adjuvant

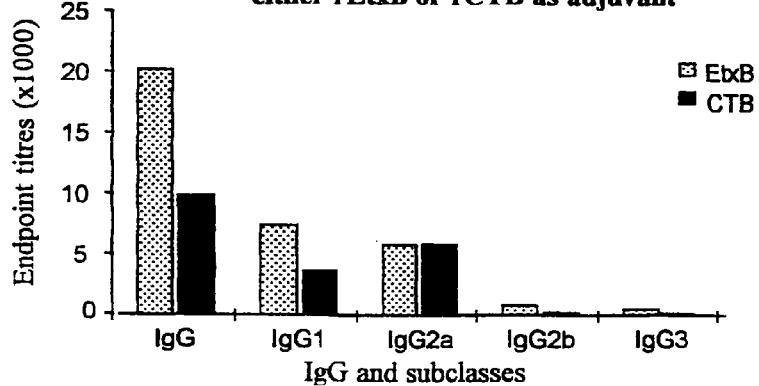

FIGURE 11

Mucosal IgA in vaginal washings following intranasal immunisation of mice with HSV-1 or mock glycoproteins (gp) alone or in the presence of adjuvant

A - HSV-1 gp only
B - HSV-1 gp + Ctx/CtxB adjuvant
C - HSV-1 gp + rEtxB adjuvant
D - HSV-1 gp + rCtxB adjuvant
E - Mock gp only Groups of mice Endpoint titre

* antibody levels were measured by ELISA and are expressed as end point titres calculated by linear regression analysis
Ctx/CtxB = 0.5µg Ctx + 10µg CtxB
rETxB = 10µg recombinant EtxB
gp = 10µg HSV-1 or mock glycoproteins as indicated.

FIGURE 12

Level of HSV-1-specific immunoglobulin in sera from mice immunised with HSV-1 glycoproteins in the presence of different doses of rEtxB as adjuvant

*antibody levels were measured by ELISA and are expressed as a percentage of the levels stimulated following ocular infection induced by scarification with $10^5$ pfu HSV-1 strain SC16.

FIGURE 13

Level of IgA in eye washings of mice immunised with HSV-1 glycoproteins in the presence of varying concentrations of rEtxB

[Bar chart: Y-axis "% standard*" from 0 to 15; X-axis "Dose of rEtxB (µg/dose)" with values 100, 50, 20, 10, 5, 1, 0.1, 0.01, 0. Bars at 100, 50, 20 are ~14; at 10 is ~7; at 5 is ~3.5; at 1 is ~1.5; at 0.1, 0.01, 0 are ~0.]

\* antibody levels were measured by ELISA and are expressed as a percentage of the levels stimulated following ocular infection induced by scarification with $10^5$ pfu HSV-1 strain SC16.

FIGURE 14

Level of IgA in vaginal washings of mice immunised with HSV-1 glycoproteins in the presence of varying concentrations of rEtxB Concentration of rEtxB µg/ml (Endpoint titre* vs concentrations: 100, 50, 20, 10, 5, 1, 0.1, .01, 0)

* antibody levels were measured by ELISA and are expressed as endpoint titres calculated using linear regression analysis.

FIGURE 15

IgG subclass distribution of the serum antibody response to HSV-1 following intransal immunisation with Ctx/CtxB or rETxB or ocular infection with HSV-1

FIGURE 16

Cytokine production from cultures of lymph node cells taken from mice which were either infected with HSV-1 by ocular scarification, or were immunised by intranasal administration of HSV-1 glycoproteins with either Ctx/CtxB or rEtxB as adjuvant

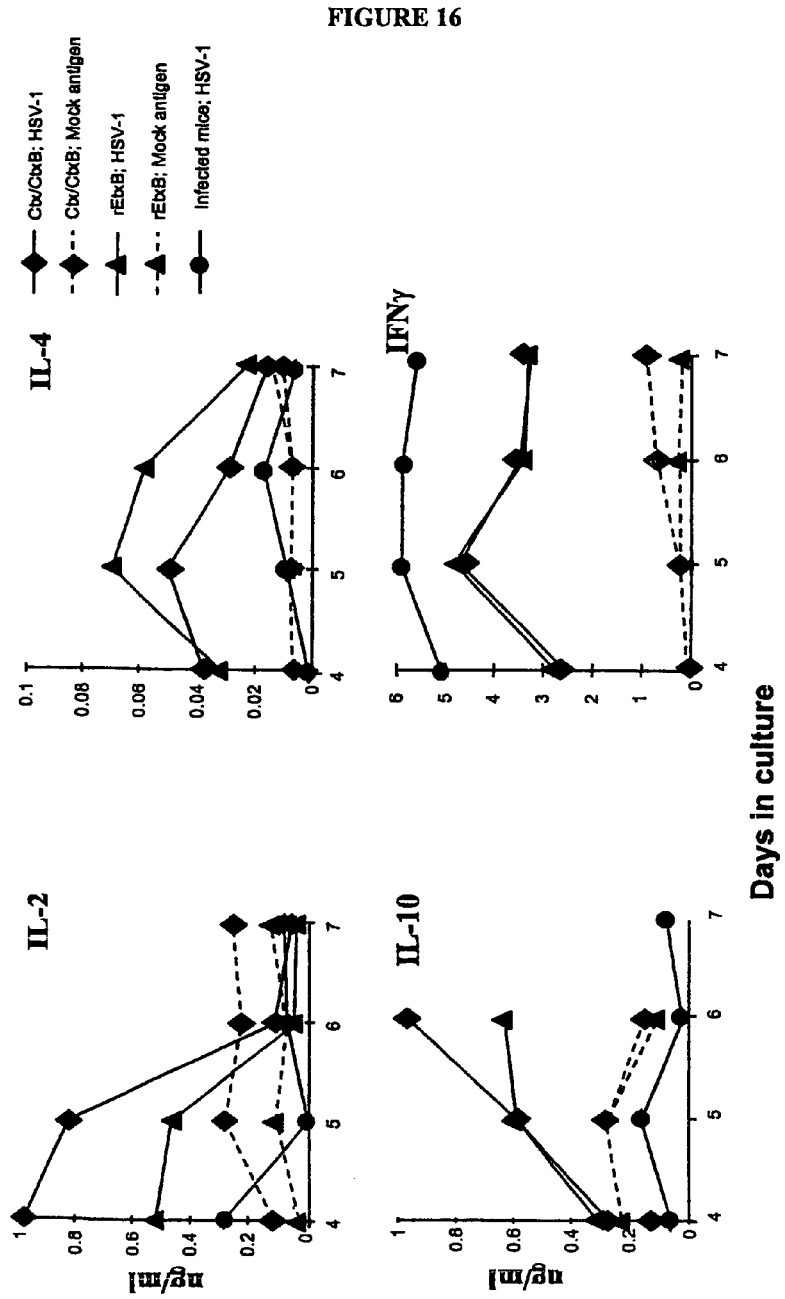

Cytokines were measured using cELISA and quantities calculated against standard curves prepared using recombinant cytokines. Values are expressed from cultures from mice immunised intranasally with 10μg HSV-1 glycoproteins with either Ctx/CtxB or rETxB as adjuvant, and cultured with whole killed HSV-1 (HSV-1) or identically treated mock virus preparation (Mock antigen).

FIGURE 17

Level of protection against ocular HSV-1 infection in mice immunised intranasally with a mixture of HSV-1 or mock glycoproteins in the presence of rEtxB as adjuvant

| Immunisation | Corneal Ulcers | Opacity/ Oedema | Lid Disease | Zosteriform Infection | Encephal- itis | Latency | | |
|---|---|---|---|---|---|---|---|---|
| | | | | | | TGI | TGII | TGIII |
| 10μg HSV-1 gp + 10μg rEtxB per dose | 69% | 10% | 0% | 3% | 0% | 22% | 11% | 0% |
| 10μg mock gp + 10μg rEtxB per dose | 80% | 68% | 74% | 72% | 50% | 83% | 30% | 16% |

[1]n=29
[2]n=30

VACCINE

CROSS-REFERENCE TO RELATED APPLICATIONS

This application is a national stage entry of PCT/GB99/01461, filed 10 May 1999, and claims priority benefits, under Title 35, United States Code §119, of GB 9809958.3, filed 8 May 1998, GB 9811954.8, filed 3 Jun. 1998, and GB 9812316.9, filed 8 Jun. 1998.

This invention relates to an immunomodulator for use in a vaccine which is intended for use against a range of infectious agents. Further this invention relates to a vaccine composition comprising the immunomodulator, preferably in combination with antigen and a vaccination method using the vaccine composition.

Cholera toxin (Ctx) and its close relative E. coli heat-labile enterotoxin (Etx) are potent immunogens and mucosal adjuvants. However, their inherent toxicity makes them unsuitable for human use. For example, although Ctx is the most commonly used mucosal adjuvant in experimental animals, it is unsuitable for use in humans because of its potent diarrhoea-inducing properties. Attempts have been made to separate toxicity from adjuvant activity, for example by using components of Ctx and Etx as replacements for the holotoxins themselves. E. coli verotoxin (Vtx) is another known bacterial toxin.

Ctx and Etx are heterohexameric proteins composed of a an enzymatically active A subunit and a pentameric B subunit. CtxB and EtxB are known to bind GM1-ganglioside (GM1), a glycosphingolipid found ubiquitously on the surface of mammalian cells. Vtx binds to Gb3 which is a similar type of receptor to GM1.

In an attempt to circumvent the problem of toxicity for vaccine development, the adjuvant activity of the non-toxic B subunits has previously been investigated. However, many of the reports describe experiments in which a commercial preparation of CtxB or EtxB was used. These preparations are inevitably contaminated with a small but biologically significant amount of active toxin, so the adjuvant activity attributable to the B subunit is indistinguishable from the adjuvant activity of the whole toxin (Wu and Russell (1993) Infection and Immunity 61: 314-322, U.S. Pat. No. 5,182,109). Subsequent studies using recombinant CtxB (rCtxB) have suggested that CtxB is a poor mucosal adjuvant and only the addition of native holotoxin can provoke strong bystander responses (Tamura et al (1994) Vaccine 12: 419-426). Other studies have suggested that rCtxB lacks the ADP-ribosylating and the cAMP-stimulating activities of the holotoxin and that, as adjuvant mechanism is linked to these abilities, CtxB would be unsuitable for use as an adjuvant (Vajdy and Lycke (1992) Immunology 75: 488-492, Lycke et al (1992) Eur. J. Immunol. 22: 2277-2281, Douce et al (1997) Infection and Immunity 65: 2821-2828).

In another study, intranasal administration of ovalbumin using rCtxB as an adjuvant resulted in poor antibody responses. A non-toxic derivative of Ctx with a mutation in the A subunit also generated weak responses to bystander antigens, whereas the presence of an active A subunit dramatically enhanced adjuvant activity, suggesting that an active A subunit is essential (Douce et al (1997) as above).

It has also been shown that rCtxB and rEtxB can be used to promote tolerance to heterologous antigens (Sun et al (1994) Proc. Natl. Acad. Sci. 91: 4610-4614, Sun et al (1996) Proc. Natl. Acad. Sci. 93: 7196-7201, Bergerot et al (1997) Proc. Natl. Acad. Sci. 94: 4610-4614, Williams et al (1997) Proc. Natl. Acad. Sci. 94: 5290-5295), suggesting that these molecules would be unsuitable for use as adjuvants.

The Basis of the Present Invention

In spite of the teaching in the art that CtxB and EtxB have poor adjuvanticity and can, in fact, act as tolerogens, the present inventors nevertheless investigated the use of rEtxB (thus containing no residual holotoxin or A subunit) in an intranasal vaccine for HSV in a murine model and surprisingly found that it is able to stimulate protective immune responses to viral challenge. Specifically, the present inventors found that:

i) agents such as EtxB and CtxB stimulate high levels of local (mucosal) antibody production (although immunization using rEtxB stimulated lower levels of overall serum antibody production than Ctx/CtxB combined);

ii) the distribution of antibodies produced was skewed towards non-complement fixing antibodies, especially S-IgA and IgG1;

iii) agents such as EtxB and CtxB also stimulated local and systemic T-cell proliferative responses;

iv) agents such as CtxB and EtxB tend to shift the immune response from a Th1-associated response to a Th2-associated response;

v) when agents such as CtxB and EtxB are used as immunomodulators some of the harmful effects of Th2-associated responses, such as the generation of IgE, are avoided;

vi) rEtxB is a more efficient immunomodulator than rCtxB;

vii) agents such as EtxB and CtxB are capable of altering the way in which an antigen presenting cell internalises and processes antigen, increasing antigen persistence;

viii) if an agent such as EtxB and CtxB is linked to an antigen, it is possible to alter the processing route of the antigen by altering the linkage to the immunomodulator; and ix) VtxB exerts similar immunomodulatory effects on leukocyte populations in vitro to those exerted by EtxB and CtxB.

These important discoveries are the basis of the various aspects of the present invention and enabled the inventors to predict that pure EtxB, CtxB and VtxB, as well as other agents capable of binding to or mimicking the effect of binding to GM1 or Gb3, will be useful as immunomodulators for use in vaccines in the prophylactic and therapeutic vaccination against HSV-1 infection, as well as other infections, the prevention or treatment of which would benefit from immunomodulation of the types listed above.

Stimulation of Immune Responses

EtxB, CtxB, VtxB and other agents capable of binding to or mimicking the effects of binding to GM1 or Gb3, are capable of acting as immunomodulators and stimulate specific immune responses to antigenic challenge.

According to a first aspect of the present invention, there is provided the use of:

(i) EtxB, CtxB or VtxB free from whole toxin;

(ii) an agent other than EtxB or CtxB, having GM1-binding activity, or an agent other than VtxB having Gb3-binding activity; or (iii) an agent having an effect on intracellular signalling events mediated by GM1-binding or Gb3 binding;

as an immunomodulator for a vaccine against infectious diseases.

According to a second aspect of the present invention, there is provided a vaccine composition for use against an infectious disease, which infectious disease is caused by an infectious agent, wherein the vaccine composition comprises an antigenic determinant and an immunomodulator selected from:

(i) EtxB, CtxB or VtxB free from whole toxin;

(ii) an agent other than EtxB or CtxB, having GM1-binding activity, or an agent other than VtxB having Gb3-binding activity; or (iii) an agent having an effect on intracellular signalling events mediated by GM1-binding or Gb3 binding;

wherein said antigenic determinant is an antigenic determinant of said infectious agent.

The antigen and immunomodulator may be linked, for example covalently or genetically linked, to form a single effective agent. In a specific embodiment of this invention the antigen and immunomodulator may be chemically conjugated. For example, the antigen and immunomodulator may be chemically conjugated using heterobifunctional cross-linking reagents. In most applications of this aspect of the invention, separate administration (in which the antigen and immunomodulator are not so linked) is preferred because it enables separate administration of the different moieties.

According to a third aspect of the present invention, there is provided a kit for vaccination of a mammalian subject, such as a human or veterinary subject, against an infectious disease, comprising:

a) one of the following agents:

(i) EtxB, CtxB or VtxB free from whole toxin;

(ii) an agent other than EtxB or CtxB, having GM1-binding activity, or an agent other than VtxB having Gb3-binding activity; or (iii) an agent having an effect on intracellular signalling events mediated by GM1-binding or Gb3 binding; and b) an antigenic determinant which is an antigenic determinant of the infectious disease, for coadministration with the said vaccine immunomodulator.

The vaccine composition of the second aspect of the invention and the kit of the third aspect of the invention may be used in a prophylactic or therapeutic vaccination method, where a "prophylactic vaccine" is administered to naive individuals to prevent disease development, and a "therapeutic vaccine" is administered to individuals with an existing infection to reduce or minimise the infection or to abrogate the immunopathological consequences of the disease.

Agents such as EtxB have the capacity to alter the nature of the immune response once infection has occurred. A therapeutic vaccine (i.e. one which need not contain antigen) comprising such an agent may find particular use in circumstances in which the immune response has failed to get rid of an infection. This application may be of particular use to treat a chronic disease, for example a disease for which the causative agent is selected from the group consisting of herpes viruses, hepatitis viruses, HIV, TB and parasites.

According to a fourth aspect of the present invention there is provided a method of preventing or treating a disease in a host, which method comprises the step of inoculating said host with a vaccine comprising at least one antigenic determinant and an immunomodulator, where the immunomodulator is:

(i) EtxB, CtxB or VtxB free from whole toxin;

(ii) an agent other than EtxB or CtxB, having GM1-binding activity, or an agent other than VtxB having Gb3-binding activity; or (iii) an agent having an effect on intracellular signalling events mediated by GM1-binding or Gb3 binding.

The vaccine may be packaged for coadministration and may be administered by a number of different routes such as intranasal, oral, intra-vaginal, urethral or ocular administration. Intranasal immunisation is presently preferred. When a vaccine is administered intranasally, it may be administered as an aerosol or in liquid form.

The antigenic determinant and immunomodulator may be administered to the subject as a single dose or in multiple doses.

In a first embodiment the immunomodulator of the first aspect of the invention, the vaccine of the second aspect of the invention, the kit of the third aspect of the invention and the method of the fourth aspect of the invention is used against a disease for which the infectious agent is a member of the herpes virus family. For example, the infectious agent may be selected from the group consisting of HSV-1, HSV-2, EBV, VZV, CMV, HHV-6, HHV-7 and HHV-8. In particular, the infectious agent may be HSV-1, HSV-2, CMV or EBV.

In this first embodiment, the antigenic determinant is preferably an antigenic determinant of an immediate early, early or late gene product (for example a surface glycoprotein) of the herpes virus.

If the infectious agent is HSV-1 or HSV-2, the antigenic determinant may be an antigenic determinant of a gene product selected from the following group: gD, gB, gH, gC or a latency associated transcript (LAT).

If the infectious agent is EBV, the antigenic determinant may be an antigenic determinant of gp340 or gp350 or of a latent protein (for example EBNAs 1, 2, 3A, 3B, 3C and -LP, LMP-1, -2A and 2B or an EBER).

In a second embodiment, the immunomodulator of the first aspect of the invention, the vaccine of the second aspect of the invention, the kit of the third aspect of the invention and the method of the fourth aspect of the invention is used against a disease for which the infectious agent is an influenza virus.

In this second embodiment, the antigenic determinant is preferably an antigenic determinant of a viral coat protein (for example haemagglutinin and neuraminidase) or of an internal protein (for example, nucleoprotein).

In a third embodiment, the immunomodulator of the first aspect of the invention, the vaccine of the second aspect of the invention, the kit of the third aspect of the invention and the method of the fourth aspect of the invention is used against a disease for which the infectious agent is a parainfluenza virus.

In a fourth embodiment, the immunomodulator of the first aspect of the invention, the vaccine of the second aspect of the invention, the kit of the third aspect of the invention and the method of the fourth aspect of the invention is used against a disease for which the infectious agent is respiratory syncytial virus.

In a fifth embodiment, the immunomodulator of the first aspect of the invention, the vaccine of the second aspect of the invention, the kit of the third aspect of the invention and the method of the fourth aspect of the invention is used against a disease for which the infectious agent is a hepatitis virus. For example, the infectious agent may be selected from the group consisting of hepatitis A, B, C and D. In particular the infectious agent may be hepatitis A or C.

In a sixth embodiment, the immunomodulator of the first aspect of the invention, the vaccine of the second aspect of the invention, the kit of the third aspect of the invention and the method of the fourth aspect of the invention is used against meningitis. In this sixth embodiment, the infectious agent may be selected from the group consisting of *Neisseria meningitidis*, *Haemophilus influenzae* type B and *Streptococcus pneumoniae*.

In a seventh embodiment, the immunomodulator of the first aspect of the invention, the vaccine of the second aspect of the invention, the kit of the third aspect of the invention and the method of the fourth aspect of the invention is used against pneumonia or a respiratory tract infection. In this seventh embodiment, the infectious agent may be selected from the group consisting of *Streptococcus pneumoniae, Legonella pneumophila* and *Mycobacterium tuberculosis.*

In an eighth embodiment, the immunomodulator of the first aspect of the invention, the vaccine of the second aspect of the invention, the kit of the third aspect of the invention and the method of the fourth aspect of the invention is used against a sexually-transmitted disease. In this eighth embodiment, the infectious agent may be selected from the group consisting of *Neisseria gonnorheae*, HIV-1, HIV-2 and *Chlamydia trachomatis.*

In an ninth embodiment, the immunomodulator of the first aspect of the invention, the vaccine of the second aspect of the invention, the kit of the third aspect of the invention and the method of the fourth aspect of the invention is used against a gastrointestinal disease. In this ninth embodiment, the infectious agent may be selected from the group consisting of enteropathogenic, enterotoxigenic and enteroinvasive *E. coli*, rotavirus, *Salmonella enteritidis, Salmonella typhi, Helicobacter pylori, Bacillus cereus, Campylobacter jejuni* and *Vibrio cholerae.*

If the infectious agent is selected from the group consisting of enteropathogenic, enterotoxigenic, enteroinvasive, enterohaemorrhagic and enteroaggregative *E. coli*, then the antigenic determinant may be an antigenic determinant of a bacterial toxin or adhesion factor.

In a tenth embodiment, the immunomodulator of the first aspect of the invention, the vaccine of the second aspect of the invention, the kit of the third aspect of the invention and the method of the fourth aspect of the invention is used against a superficial infection. In this tenth embodiment, the infectious agent may be selected from the group consisting of *Staphylococcus aureus, Streptococcus pyogenes* and *Streptococcus mutans.*

In an eleventh embodiment, the immunomodulator of the first aspect of the invention, the vaccine of the second aspect of the invention, the kit of the third aspect of the invention and the method of the fourth aspect of the invention is used against a parasitic disease. In this eleventh embodiment, the infectious agent may be selected from the group consisting of malaria, *Trypanasoma* spp., *Toxoplasma gondii, Leishmania donovani* and *Oncocerca* spp.

Stimulation of Mucosal Immune Responses

EtxB, CtxB, VtxB and other agents capable of binding to or mimicking the effects of binding to GM1 or Gb3, are capable of specifically upregulating mucosal antibody production.

The vaccine immunomodulator of the first aspect of the invention, the vaccine composition of the second aspect of the invention and the kit of the third aspect of the invention are particularly effective against diseases where protection from infection or treatment is effected in vivo by a mucosal immune response. For example, against diseases in which, during infection, the infectious agent binds to, colonises or gains access across the mucosa. Examples of such diseases include, diseases caused by viruses (HIV, HSV, EBV, CMV, influenza, measles, mumps, rotavirus etc), diseases caused by bacteria (*E. coli, Salmonella, Shigella, Chlamydia, N. gonnorhoea, T. pallidium, Streptococcus* species including those which cause dental caries), and diseases caused by parasites.

In a preferred embodiment of the second aspect of the present invention there is provided a vaccine against HSV-1 infection comprising at least one HSV-1 antigenic determinant and an immunomodulator, where the immunomodulator is:

(i) EtxB, CtxB or VtxB free from whole toxin;
(ii) an agent other than EtxB or CtxB, having GM1-binding activity, or an agent other than VtxB having Gb3-binding activity; or
(iii) an agent having an effect on intracellular signalling events mediated by GM1-binding or G3b binding.

Preferably the immunomodulator is EtxB.

In a preferred embodiment of the third aspect of the present invention there is provided a kit for vaccination of a mammalian subject against an HSV-1, comprising:

a) a vaccine immunomodulator which is:
(i) EtxB, CtxB or VtxB free from whole toxin;
(ii) an agent other than EtxB or CtxB, having GM1-binding activity, or an agent other than VtxB having Gb3-binding activity; or
(iii) an agent having an effect on intracellular signalling events mediated by GM1-binding or G3b binding; and
b) at least one HSV-1 antigenic determinant, for coadministration with the said vaccine immunomodulator.

According to a fifth aspect of the invention there is provided the use of:

(i) EtxB, CtxB or VtxB free from whole toxin;
(ii) an agent other than EtxB or CtxB, having GM1-binding activity, or an agent other than VtxB having Gb3-binding activity; or
(iii) an agent having an effect on intracellular signalling events mediated by GM1-binding or Gb3 binding to upregulate the production of antibodies at mucosal surfaces. The production of non-complement-fixing serum antibodies may also be upregulated. Preferably, S-IgA is produced in accordance with the fifth aspect of the invention.

In this fifth aspect of the present invention, the agent may be used in conjunction with one or more antigenic determinant(s).

Downregulating the Pathological Components of Immune Responses

The inventors also found that when pure EtxB was used as an immunomodulator in the described way, the harmful effects of Th2 associated responses, such as the generation of high levels of potentially pathological IgE, were avoided. Despite this, the immune response triggered by the use of EtxB (or CtxB or VtxB) as an immunomodulator appears to favour the induction of Th2-associated cytokines. In other words EtxB (or CtxB) induces a shift from a Th1- to a Th2-type response. This has enabled the inventors to predict that pure EtxB, CtxB or VtxB, as well as other agents capable of binding to or mimicking the effect of binding to GM1 or Gb3, will be capable of down regulating pathological components of the immune response associated with both Th1 and Th2 activation.

According to a sixth aspect of the present invention, there is provided the use of:

(i) EtxB, CtxB or VtxB free from whole toxin;
(ii) an agent other than EtxB or CtxB, having GM1-binding activity, or an agent other than VtxB having Gb3-binding activity; or
(iii) an agent having an effect on intracellular signalling events mediated by GM1-binding or Gb3 binding;

to downregulate the pathological components of Th2-associated immune responses. The pathological components of Th1-associated immune responses may also be down-regulated.

It is known that EtxB and CtxB bind to GM1 and induce differential effects on lymphocyte populations, including a specific depletion of CD8+ T cells and an associated activation of B cells (WO 97/02045). Hence, EtxB and CtxB are thought to alter the balance of the immune response such that inflammatory Th1 associated reactions are down-regulated while Th2 associated responses are upregulated. Th1 responses include the secretion of γIFN by activated T-cells leading to macrophage activation and delayed type hypersensitivity reactions. Such responses may be an important cause of pathology during infections with a number of pathogens. Th2 responses include the activation of T-cells to produce cytokines such as IL-4, IL-5, IL-10, and are known to promote the secretion of high levels of antibody, especially IgA.

It has now surprisingly been found that when EtxB is used as an immunomodulator in the described way, the harmful effects of Th2 associated responses, such as the generation of high levels of potentially pathological IgE, are avoided. Therefore, EtxB and CtxB are capable of down regulating pathological components of the immune response associated both with Th1 and Th2 activation. Such responses are modulated in favour of the production of high levels of non-complement fixing serum antibodies and secretory IgA production at the mucosal surfaces.

The use of an agent in accordance with the sixth aspect of the invention is particularly useful for therapeutic vaccination in diseases in which immunopathological mechanisms are involved. Examples of such diseases are HSV-1, HSV-2, TB and HIV.

The first and sixth aspects of the invention can be combined. In other words, agents such as EtxB can be used simultaneously as an immunomodulator and a therapeutic agent. For example in diseases where immunopathological mechanisms are involved, the use of a vaccine incorporating agents such as EtxB or CtxB may act not only to limit infection, but also to abrogate the pathological disease processes. The immunomodulating agent is thus acting both prophylactically and therapeutically. Examples of infections where vaccination in this way is therefore likely to be of particular value include those caused by the herpes virus family, gastrointestinal and respiratory tract pathogens.

Immunomodulation of the Antigen Processing Pathway
a) Prolonging Presentation

The present inventors have also found that when EtxB (or CtxB or VtxB) is used as an immunomodulator, the antigen internalisation and processing pathway is altered. The presence of the B subunit causes prolonged presentation, possibly by altering antigen trafficking inside the antigen presenting cell such that antigen degradation is delayed and therefore maintained over longer periods. This feature of B-subunit associated antigen presentation means that vaccines incorporating an agent in accordance with the present invention will have increased antigen persistence and lead to sustained immunological memory.

According to a seventh aspect of the present invention, there is provided the use of:
 (i) EtxB, CtxB or VtxB free from whole toxin;
 (ii) an agent other than EtxB or CtxB, having GM1-binding activity, or an agent other than VtxB having Gb3-binding activity; or
 (iii) an agent having an effect on intracellular signalling events mediated by GM1-binding or Gb3 binding;
 as an immunomodulator in a vaccine, to prolong antigen presentation and give sustained immunological memory in a mammalian subject.

According to an eighth aspect of the present invention, there is provided a vaccine composition for use against an infectious disease, comprising an antigenic determinant and a immunomodulator selected from:
 (i) EtxB, CtxB or VtxB free from whole toxin;
 (ii) an agent other than EtxB or CtxB, having GM1-binding activity, or an agent other than VtxB having Gb3-binding activity; or
 (iii) an agent having an effect on intracellular signalling events mediated by GM1-binding or Gb3 binding;
 wherein said antigenic determinant is an antigenic determinant of said infectious disease and wherein the immunomodulator prolongs presentation of the antigenic determinant and gives sustained immunological memory.

b) Intracellular Targeting of the Antigen to a MHC-I or MHC-II Associated Pathway As aforementioned, the antigen and immunomodulator in a therapeutic or prophylactic vaccine may be linked, for example covalently or genetically linked, to form a single effective agent. The present inventors have found that is possible to direct the antigen to different compartments of the cell and hence to different antigen presentation pathways by altering the linkage of the antigen to the immunomodulator.

By linking the antigen or antigenic determinant to the immunomodulator in a certain way, it is possible to facilitate translocation of the antigen across the endosomal membrane into the cytosol. The present inventors predict that this would enhance loading of antigenic peptides on to MHC class I molecules. The use of an antigen-immunomodulator conjugate can therefore be used to specifically enhance the activation of cytotoxic T cells (CTL). Induction of CTL is beneficial for the prevention and treatment of many diseases especially those caused by viruses, intracellular bacteria and parasites.

The linkage of the antigen-immunomodulator conjugate can also be chosen so that the antigen is delivered into the nucleus.

According to a ninth aspect of the present invention there is provided a conjugate comprising an antigen or antigenic determinant and an immunomodulator selected from:
 (i) EtxB, CtxB or VtxB free from whole toxin;
 (ii) an agent other than EtxB or CtxB, having GM1-binding activity, or an agent other than VtxB having Gb3-binding activity; or
 (iii) an agent which has an effect on vesicular internalisation mediated by GM1-binding or Gb3 binding.

According to a tenth aspect of the present invention there is provided a vaccine composition for use against an infectious disease, which infectious disease is caused by an infectious agent, which vaccine composition comprises a conjugate of an antigen or antigenic determinant and an immunomodulator selected from:
 (i) EtxB, CtxB or VtxB free from whole toxin;
 (ii) an agent other than EtxB or CtxB, having GM1-binding activity, or an agent other than VtxB having Gb3-binding activity; or
 (iii) an agent which has an effect on vesicular internalisation mediated by GM1-binding or G3b binding;
 wherein said antigen or antigenic determinant is an antigen or antigenic determinant of said infectious agent.

The antigen or antigenic determinant may be linked to the immunomodulator by a variety of methods including genetic linkage or chemical conjugation. In a first preferred embodiment the conjugate is a fusion protein made by genetic linkage of the antigen or antigenic determinant to the immunomodulator. Preferably the antigen or antigenic determinant is genetically linked to the C-terminus of the immunomodulator. In a second preferred embodiment the antigen or antigenic determinant is chemically conjugated to the immunomodulator. Preferably the antigen or antigenic determinant is conjugated to the immunomodulator using a bifunctional cross-linking reagent, such as a heterobifunctional cross-linking reagent. More preferably the cross-linking agent is N-γ(-maleimido-butyroxyl)-succinimide ester (GMBS) or N-succinimidyl-(3-pyridyl-dithio)-propionate (SPDP). The vaccine composition may be administered by a number of different routes such as intranasal, oral, intra-vaginal, urethral or ocular administration. Intranasal immunisation is preferred.

According to an eleventh aspect of the present invention there is provided the use of:
(i) EtxB, CtxB or VtxB free from whole toxin;
(ii) an agent other than EtxB or CtxB, having GM1-binding activity, or an agent other than VtxB having Gb3-binding activity; or
(iii) an agent which has an effect on vesicular internalisation mediated by GM1-binding or Gb3 binding;
in a conjugate with antigen or antigenic determinant to target the delivery or said antigen or antigenic determinant to the cytosol or nucleus of an antigen presenting cell.

According to a twelfth aspect of the present invention there is provided the use of:
(i) EtxB, CtxB or VtxB free from whole toxin;
(ii) an agent other than EtxB or CtxB, having GM1-binding activity, or an agent other than VtxB having Gb3-binding activity; or
(iii) an agent which has an effect on vesicular internalisation mediated by GM1-binding or Gb3 binding;
in a conjugate with antigen or antigenic determinant to upregulate the presentation of said antigenic determinant, or an antigenic determinant derived from said antigen, by MHC class 1 molecules.

Preferably the use of the conjugate of the twelfth aspect of the invention is used is combination with the use of the agent in accordance with the fifth aspect of the invention to stimulate strong CTL responses and to upregulate mucosal antibody production. This activity would be particularly useful in the prevention and treatment of viral infections, for example influenza.

EtxB is the Preferred Immunomodulator

It has previously been thought that EtxB and CtxB have similar properties. However, the present inventors have found that rEtxB is a more potent and efficient immunomodulator than rCtxB. Hence the preferred immunomodulator is EtxB, or agents which mimic the effects of EtxB.

EBV

EBV is one of the eight known human herpes viruses. Infection usually occurs in early childhood; however, clinical symptoms are usually weak or undetectable at this stage. Primary infection with EBV later in life is associated with infectious mononucleosis (IM), which is the second most frequent disease in adolescence in the US. EBV also has oncogenic potential. There is a strong link between EBV and endemic Burkitt's lymphoma (BL) and undifferentiated nasopharyngeal carcinoma (NPC). Also, a large proportion of lymphomas that occur in immuno-compromised patients are caused by EBV, and an association has been shown to exist between certain Hodgkin's lymphomas and EBV.

Latently EBV-infected cells express a small number of so-called "latent" proteins. These include six nuclear proteins (EBNAs 1, 2, 3A, 3B, 3C and -LP), three integral membrane proteins (LMP-1, 2A and 2B) and two non-polyadenylated virus derived RNAs (EBERs) with a role in RNA splicing.

EBV latent membrane protein 1 (LMP-1) is present in the plasma membrane of infected cells. It is also expressed in nasopharyngeal carcinomas (NPCs) and EBV-positive Hodgkin's lymphomas (HD) which indicates a role for LMP-1 in the development of these tumours. The LMP-1 gene can alter the phenotype of uninfected cells causing the upregulation of cell surface activation markers, promoting cell proliferation. LMP-1 can also alter signalling pathways and has anti-apoptotic effects. An cellular immune response directed against this viral antigen has not been demonstrated with any degree of certainty in either healthy carriers or tumour patients.

Many animal viruses have evolved mechanisms to avoid detection by the host immune system. Commonly, these mechanisms involve interference with the TAP-associated peptide translocation system. It is thought that EBV has also evolved similar mechanisms to avoid immune system detection, thus allowing its persistence in the host. This explains why certain cellular immune responses are not detectable to the EBV latent protein EBNA1 and could explain the apparent absence of such responses against LMP1.

According to an thirteenth aspect of the invention there is provided a vaccine composition which comprises:
a) one of the following agents:
(i) EtxB, CtxB or VtxB free from whole toxin;
(ii) an agent other than EtxB or CtxB, having GM1-binding activity, or an agent other than VtxB having Gb3-binding activity; or
(iii) an agent having an effect on intracellular signalling events mediated by GM1-binding or Gb3 binding; and
b) an EBV antigen
for use in the treatment and/or prevention of EBV-associated diseases.

In particular the vaccine composition of the thirteenth aspect of the invention comprises EtxB, CtxB, or an agent other than EtxB or CtxB which has GM1-binding activity.

According to a fourteenth aspect of the invention there is provided a therapeutic composition which comprises:
(i) EtxB, CtxB or VtxB free from whole toxin;
(ii) an agent other than EtxB or CtxB, having GM1-binding activity, or an agent other than VtxB having Gb3-binding activity; or
(iii) an agent having an effect on intracellular signalling events mediated by GM1-binding or Gb3 binding;
for use in the treatment of EBV-associated diseases.

In particular the therapeutic composition of the fourteenth aspect of the invention comprises EtxB, CtxB, or an agent other than EtxB or CtxB which has GM1-binding activity.

Based on the knowledge that EtxB cocaps with LMP1, and that EtxB promotes fragmentation of LMP-1, it is theorised that EtxB (and other agents like CtxB having GM1 binding activity) will be useful to stimulate anti-EBV immune responses. This activity has applications in vaccines to prevent EBV associated diseases, and in therapeutic treatments to treat such diseases once they have developed.

Without wishing to be bound by theory, it is believed that when EtxB cocaps with LMP-1 the antigen is processed by a different intracellular route, which enables the antigen to by-pass the normal processing route which is blocked by the virus. The antigen is thus presented efficiently on the cell surface. The action of EtxB may also cause different epitopes of the antigen to be presented at the cell surface, from those which are presented if the antigen were processed by the conventional route.

The vaccine of the thirteenth aspect of the invention may be used to prevent infection by EBV, or development of EBV-associated diseases in EBV-infected individuals. The vaccine may also comprise a separate adjuvant, or the agent (such as EtxB or CtxB) can act as an adjuvant in its own right.

The agents specified in the fourteenth aspect of the present invention may be used alone (i.e. without antigen) in the treatment of a EBV-associated disease which has already developed in a subject.

The preferred agent for use in the thirteenth and fourteenth aspects of the invention is EtxB.

The EBV antigen is an antigen derivable from EBV itself or an antigen which is caused to be expressed by an EBV-infected host cell by the action of EBV. Preferably the antigen is an EBV latent membrane protein. Particularly preferred are the antigens LMP-1, LMP-2A, LMP-2B, and EBNA-1 as well as antigenic fragments thereof. The antigen may be isolated directly from EBV infected cells, or be made by synthetic or recombinant means.

The thirteenth and fourteenth aspects of present invention are particularly suited for the treatment and/or prevention of the following diseases: infectious mononucleosis, Burkitt's lymphoma, nasopharyngeal carcinomas, and Hodgkin's lymphomas. It is believed that these aspects of the invention will be particularly suited to the treatment and/or prevention of nasopharyngeal carcinomas and Hodgkin's lymphomas.

The vaccine or the therapeutic composition according to the thirteenth and fourteenth aspects of the invention may be used to prevent development of, or treat, an EBV-associated disease in a mammalian subject, by administration of an immunologically effective amount to the subject.

The mammalian subject may be, for example, a healthy EBV-infected or uninfected individual, an immunodeficient individual, or an individual with an EBV-associated disease.

The vaccine may be administered by any suitable route. The agent and the antigen may be co-administered to the mammalian subject or administered separately. The agent and the antigen may be separate or linked, for example covalently or genetically linked, to form a single effective agent.

GM-1 and Gb3-Associated Signalling

Without wishing to be bound by theory, it is believed that GM1 or Gb3 binding may trigger intracellular signalling directly or indirectly. The present inventors have also found evidence which suggests that EtxB interacts with at least one other receptor which is involved in the GM1 associated intracellular signalling event. It may be that binding of EtxB (or CtxB) to GM1 facilitates binding to a protein, which protein triggers intracellular signalling. It is not known what specifically triggers the signalling event, it may be phosphorylation of GM1 or the protein. When EtxB/CtxB binds GM1 on the cell surface, bound GM1 is internalised in vesicles (Williams et al (1999) Immunology Today 20; 95-101). GM1 and other glycolipids (such as Gb3) are known to be preferentially located in "membrane rafts" in which key protein receptors are also found. It is therefore possible that internalisation of GM1 as a result of B-subunit binding causes cocapping of such proteins leading to their being triggered to mediate intracellular signalling events.

Definitions

An adjuvant is a substance which non-specifically enhances the immune response to an antigen, as distinct from a vaccine carrier, the purpose of which is to target the antigen to a desired site. The term "immunomodulator" is used herein to indicate an agent which acts, like an adjuvant, to stimulate certain immune responses, but which also directs the immune response in a particular direction.

The term "coadministration" is used to mean that the site and time of administration of the antigen and immunomodulator are such that the necessary immune response is stimulated. Thus, while the antigen and the immunomodulator may be administered at the same moment in time and at the same site, there may be advantages in administering the antigen at a different time and/or at a different site from the immunomodulator. For example, antigen and immunomodulator may be administered together in a first step and then the immune response may be boosted in a second step by administration of antigen alone.

The term "antigenic determinant" as used herein refers to a site on an antigen which is recognised by an antibody or T-cell receptor. Preferably it is a short peptide derived from or as part of a protein antigen, however the term is also intended to include glycopeptides and carbohydrate antigenic determinants. The term also includes modified sequences of amino acids or carbohydrates which stimulate responses which recognise the whole organism.

There are a number of known methods by which it is possible to identify antigenic determinants for a given infectious agent.

For example, potential protective antigens may be identified by elevating immune responses in infected or convalescent patients, in infected or convalescent animals, or by monitoring in vitro immune responses to antigen containing preparations. For example, i) serum samples from infected or convalescent patients or infected or convalescent animals may be screened against whole cell lysates of an infectious agent, or lysates of cells infected by the said agent, by the standard technique of Western blotting to detect those antigen(s) recognised by the immune serum;

ii) serum samples from infected or convalescent patients or infected or convalescent animals may be screened against partial or highly purified antigens from an infectious agent, or lysates of cells infected by the said agent, by the standard technique s of ELISA, in which partial or highly purified antigens are used to coat microtitre wells, or by immuno blotting to detect those antigen(s) recognised by the immune sera;

iii) serum samples from infected or convalescent patients or infected or convalescent animals may be screened against whole cell lysates derived from recombinant expression systems encoding one or more antigens of interest, and using the standard techniques of ELISA or Western blotting to detect those antigen(s) recognised by the immune serum;

iv) serum samples from infected or convalescent patients or infected or convalescent animals may be screened against an expression library containing cloned genes from the infectious agent of interest, using colony blot immunodectection to identify that clones expressing antigens, or fragments thereof, that are recognised by the immune serum; or v) PBLs from the blood of infected or convalescent patients or PBL's, lymph node cells, spleen cells, or lamina propria cells from infected or convalescent animals may be cultured in vitro in the presence of partial or highly purified antigens derived from either an infectious agent, or lysates of cells infected by the said agent, or a recombinant expression system encoding one or more antigens, so as detect antigen-specific T-cell proliferative responses.

Alternatively it is possible to detect gene products which are essential for the in vivo survival of pathogens, as exemplified by the technique of signature tagged mutagenesis developed by Holden or the detection of gene products specifically induced in vivo, such as IVET (In Vivo Expression Technology) developed by Mekalanos or differential fluorescence induction developed by Falkow, identify a subset of genes amongst which are likely to potential protective antigens. Using these methods the gene products may be screened as outlined above. The genes may be cloned into expression vectors and the antigens recovered for inclusion into vaccine formulations together with agents that modulate a glycosphingolipid-associated activity.

There are a number of known methods by which it is possible to isolate antigens for a given infectious agent.

For example, surface components of an infectious agent comprising one or more potential protective antigens may be extracted from the agent, or from cells infected by the agent, by use of procedures that allow the recovery of the antigens. This may include the use of cell disruption techniques to lyse cells such as sonication and/or detergent extraction. Centrifugation, ultrafiltration or precipitation may be used on collected antigen preparations. The antigen preparation containing HSV-1 glycoproteins described in Richards et al., (1998) J. Infect. Dis. 177; 1451-7, exemplifies such a method.

Also, antigens of an infectious agent, or from cells infected by a said agent may be extracted by a variety of procedures, including but not limited to, urea extraction, alkali or acid extraction, or detergent extraction and then subjected to chromatographic separation. Material recovered in void or elution peaks comprising one or more potential protective antigens may used in vaccine formulations.

Alternatively, genes encoding one or more potential protective antigens may be cloned into a variety of expression vectors suitable for antigen production. These may include bacterial or eukaryotic expression systems, for example *Escherichia coli, Bacillus* spp., *Vibrio* spp. *Sacarromyces cerevisiae*, mammalian and insect cell lines. Antigens may be recovered by conventional extraction, separation and/or chromatographic procedures.

The terms "CtxB", "EtxB" and "VtxB" as used herein include natural and recombinant forms of the molecule. The recombinant form is particularly preferred. The recombinant form of the molecule may be produced by a method in which the gene or genes coding for the specific polypeptide chain (or chains) from which the protein is formed, is inserted into a suitable vector and then used to transfect a suitable host. For example, the gene coding for the polypeptide chain from which the EtxB assemble may be inserted into, for example, plasmid pMM68, which is then used to transfect host cells, such as *Vibrio* sp.60. The protein is purified and isolated in a manner known per se. Mutant genes expressing active mutant CtxB, EtxB or VtxB protein may be produced by known methods from the wild type gene.

The terms "CtxB", "EtxB" and "VtxB" also include mutant molecules and other synthetic molecules (containing parts of CtxB, EtxB or VtxB) which retain the capacity to bind GM1 or Gb3 or the capacity to mimic the effects of binding to GM1 or Gb3.

Agents other than EtxB and CtxB which retain GM1 binding activity, and agents other than VtxB which retain Gb3 binding activity include antibodies which bind GM1 or Gb3.

For the production of antibodies, various hosts including goats, rabbits, rats, mice, etc. may be immunized by injection with GM1 or Gb3 or any derivative or homologue thereof. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guerin) and *Corynebacterium parvum* are potentially useful human adjuvants.

Humanised monoclonal antibodies may be preferred in the present invention. Monoclonal antibodies may be prepared using any technique which provides for the production of antibody molecules by continuous cell lines in culture. These include, but are not limited to, the hybridoma technique originally described by Koehler and Milstein (1975 Nature 256: 495-497), the human B-cell hybridoma technique (Kosbor et al (1983) Immunol Today 4:72; Cote et al (1983) Proc Natl Acad Sci 80:2026-2030) and the EBV-hybridoma technique (Cole et al (1985) Monoclonal Antibodies and Cancer Therapy, Alan R Liss Inc, pp 77-96). In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851-6855; Neuberger et al (1984) Nature 312:604-608; Takeda et al (1985) Nature 314:452-454). Alternatively, techniques described for the production of single chain antibodies (U.S. Pat. No. 4,946,779) can be adapted to produce target interaction component specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for GM1 or Gb3 may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse W D et al (1989) Science 256:1275-128 1).

Peptide libraries or organic libraries may be made by combinatorial chemistry and then screened for their ability to bind GM1/Gb3. Synthetic compounds, natural products, and other sources of potentially biologically active materials can be screened in a number of ways deemed to be routine to those of skill in the art.

GM1 or Gb3 or fragments thereof can be used for screening peptides or molecules in any of a variety of screening techniques. The molecule may be free in solution, affixed to a solid support, borne on a cell surface, or located intracellularly. The abolition of activity or the formation of binding complexes between GM1 or Gb3 and the agent being tested may be measured.

Another way of determining binding to GM1/Gb3 would be by using purified GM1/Gb3 to coat microtiter plates. Following blocking, the agent under investigation is applied to the plate and allowed to interact prior to washing and detection with specific antibodies to said agent. Conjugation of the antibodies either directly or indirectly to an enzyme or radiolabel allows subsequent quantification of binding either using colorimetric or radioactivity based methods (ELISA or RIA respectively).

Another way of determining binding to GM1/Gb3 would be by binding the saccharide moiety of GM1/Gb3 to a suitable column matrix in order to allow standard affinity chromatography to be performed. Removal of known compounds applied to the column from the diluent would be used as evidence for binding activity, or alternatively, where mixtures of compounds are applied to the column, elution and subsequent analysis would determine the properties of the ganglioside binding agent. In the case of proteins, analysis would involve peptide sequencing and tryptic digest mapping followed by comparisons with available databases. In the event that eluted proteins cannot be identified in this way then standard biochemical analysis, for example mass determination by laser desorption mass spectrometry would be used to further characterise the compound. Non-proteins eluted from GM1-affinity columns would be analysed by HPLC and mass spectrometry of single homogenous peaks.

Another way of determining the ability to bind to GM1/Gb3 and the precise affinity of the interaction would be by using plasmon surface resonance as previously reported [Kuziemko et al (1996) Biochem 35:6375-6384].

Alternatively, phage display can be employed in the identification of candidate agents which bind GM1 or Gb3.

Phage display is a protocol of molecular screening which utilises recombinant bacteriophage. The technology involves transforming bacteriophage with a gene that encodes an appropriate ligand (in this case a candidate agent) capable of reacting with GM1/Gb3 (or a derivative or homologue thereof) or the nucleotide sequence (or a derivative or homologue thereof) encoding same. The transformed bacteriophage (which preferably is tethered to a solid support) expresses the appropriate ligand (such as the candidate agent) and displays it on their phage coat. The entity or entities (such as cells) bearing the target molecules which recognises the candidate agent are isolated and amplified. The successful candidate agents are then characterised. Phage display has advantages over standard affinity ligand screening technologies. The phage surface displays the candidate agent in a three dimensional configuration, more closely resembling its naturally occurring conformation. This allows for more specific and higher affinity binding for screening purposes.

Another technique for screening provides for high throughput screening of agents having suitable binding affinity to GM1 or Gb3 and is based upon the method described in detail in WO 84/03564. In summary, large numbers of different small peptide test compounds are synthesized on a solid substrate, such as plastic pins or some other surface. The peptide test agents are reacted with the target interaction component fragments and washed. A bound target interaction component is then detected—such as by appropriately adapting methods well known in the art. A purified target interaction component can also be coated directly onto plates for use in the aforementioned drug screening techniques. Alternatively, non-neutralizing antibodies can be used to capture the peptide and immobilize it on a solid support.

In all aspects of the invention, the agent having GM1-binding activity or Gb3 binding activity may also be capable of cross-linking GM1 or Gb3 receptors. EtxB is one such agent which is capable of cross-linking GM1 receptors by virtue of its pentameric form.

There are various methods for identifying agents which have an effect on intracellular signalling events mediated by GM1/Gb3 binding but which do not themselves bind GM1 or Gb3. For example, if an agent is shown to upregulate CD25 or MHC class II on B cells, or to upregulate CD25 or promote apoptosis of CD8+ T cells, or to upregulate IL-10 secretion by monocytes, but the agent is shown not to bind GM1 or Gb3 (by, for example, one of the binding assays described above), then it can be concluded that the agent is capable of mimicking the effect of GM1/Gb3 binding.

The invention will now be illustrated by reference to the accompanying drawings and the following examples.

The examples refer to the figures in which:

FIG. 1: shows the stimulation of total Ig and IgA in the serum (MS) and IgA in the eye washings (EW) in mice immunised with HSV-1 glycoproteins/rEtxB.

FIG. 2: shows T cell proliferation of (mesenteric lymph node) MLN or (cervical lymph node) CLN lymphocytes in mice immunised with HSV-1/rEtxB.

FIG. 3: shows T cell proliferation of cells from MLN and CLN of mice immunised intranasally with HSV-1 Gp in the presence of 1-20 µg EtxB.

FIG. 4: shows the level of anti-HSV-1 serum Ig in mice following administration of HSV-1 glycoproteins three times at 10 day intervals with variable amounts of rEtxB or rCtxB as adjuvant.

FIG. 5A shows the reduction in the incidence of virus shedding in mice immunized with HSV-1/rEtxB.

FIG. 5B shows the reduction in the incidence of clinical disease and latency in mice immunized with HSV-1/rEtxB.

FIG. 6: shows the Ig isotype distribution in MS following infection with HSV-1 or immunisation with HSV-1 Gp in the presence of EtxB or CtxB as immunomodulator.

FIG. 7: shows the distribution of Ig subclasses following intranasal administration of HSV-1 Gp with either rEtxB or rCtxB as immunomodulator.

FIG. 8: shows the immunogenic effect of different amounts of rEtxB or rCtxB on the level of HSV-1 specific IgA in eye washings following administration with HSV-1 glycoproteins.

Figure 9:
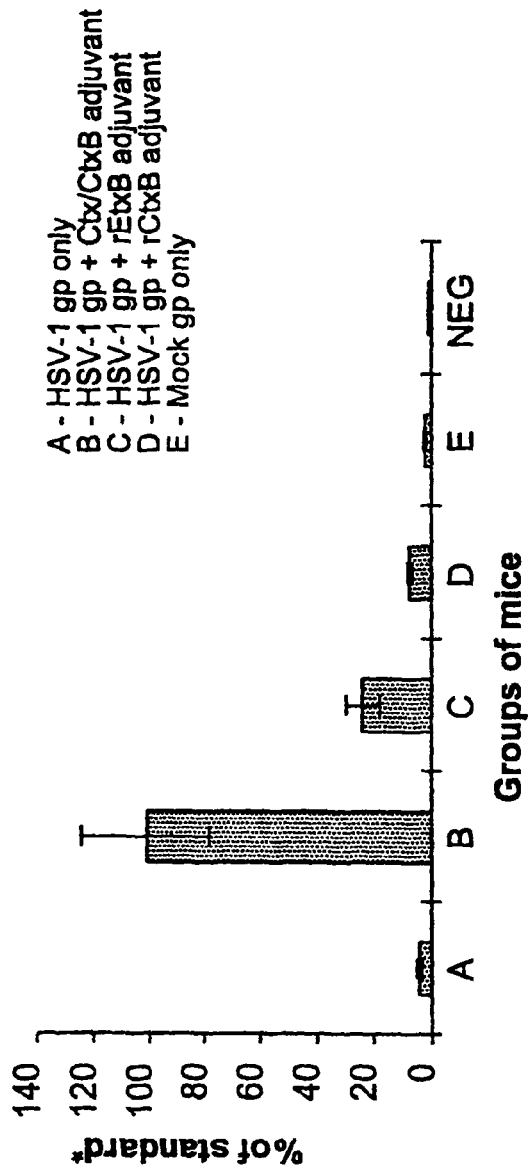

FIG. 9: shows serum immunoglobulin response following immunisation of mice with HSV-1 or mock glycoproteins (gp) alone or in the presence of adjuvant.

Figure 10:
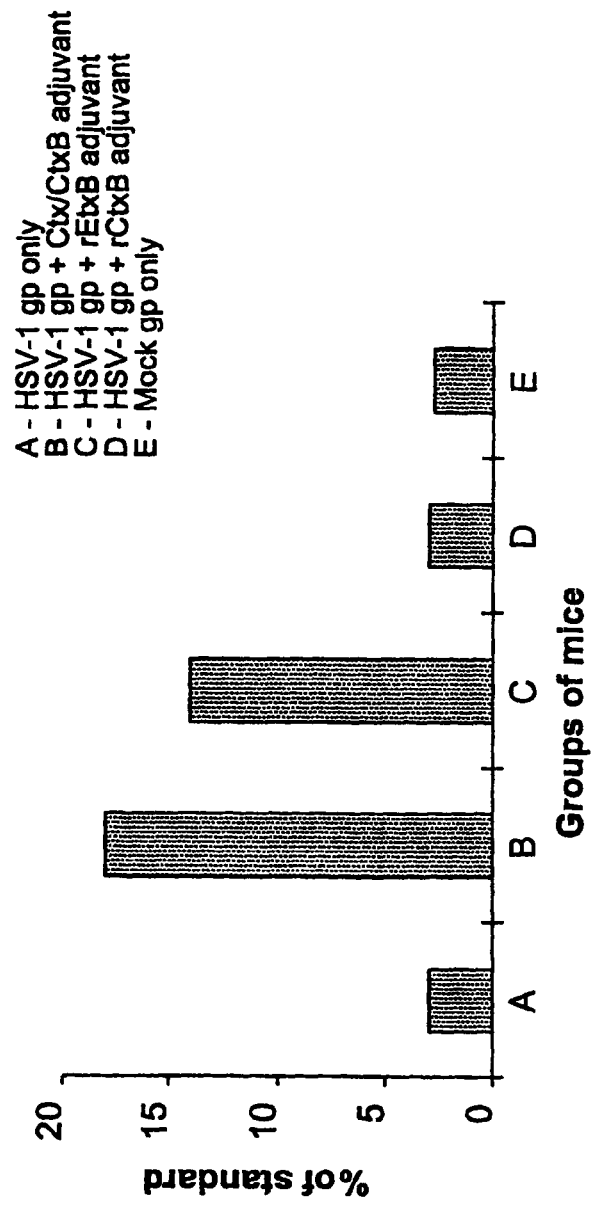

FIG. 10: shows mucosal IgA in eye washings following intranasal immunisation of mice with HSV-1 or mock glycoproteins alone or in the presence of adjuvant.

FIG. 11: shows mucosal IgA in vaginal washings following intranasal immunisation of mice with HSV-1 or mock glycoproteins (gp) alone or in the presence of adjuvant.

FIG. 12: shows the level of HSV-1-specific immunoglobulin in sera from mice immunised with HSV-1 glycoproteins in the presence of different doses of rEtxB as adjuvant.

FIG. 13: shows the level of IgA in eye washings of mice immunised with HSV-1 glycoproteins in the presence of varying concentrations of rEtxB.

FIG. 14: shows the level of IgA in vaginal washings of mice immunised with HSV-1 glycoproteins in the presence of varying concentrations of rEtxB FIG. 15: shows IgG subclass distribution of the serum antibody response to HSV-1 following intranasal immunisation with Ctx/CtxB or rEtxB or ocular infection with HSV-1.

FIG. 16: shows cytokine production from cultures of lymph node cells taken from mice which were either infected with HSV-1 by ocular scarification, or were immunised by intranasal administration of HSV-1 glycoproteins with Ctx/CtxB or rEtxB as adjuvant.

FIG. 17: shows the level of protection against ocular HSV-1 infection in mice immunised intranasally with a mixture of HSV-1 or mock glycoproteins in the presence of rEtxB as immunomodulator.

EXAMPLE 1 rEtxB can be Used in Conjunction with HSV-1 Gp for Immunisation

Mice were immunized intranasally three times with 10 µg HSV-1 glycoproteins (Gp) with either 10 or 20 µg rEtxB. Controls were either unmanipulated or given a mock preparation of viral glycoprotein (mock) derived from HIV-uninfected tissue culture cells. Antibody levels are expressed as a percentage of post-infection levels. The production of total Ig and IgA in the serum and IgA in eye washings was stimulated by HSV-1 glycoproteins/rEtxB (FIG. 1). The present inventors have also shown that doses of rEtxB as low as 0.1 µg are also effective at stimulating such responses.

Figure 2:
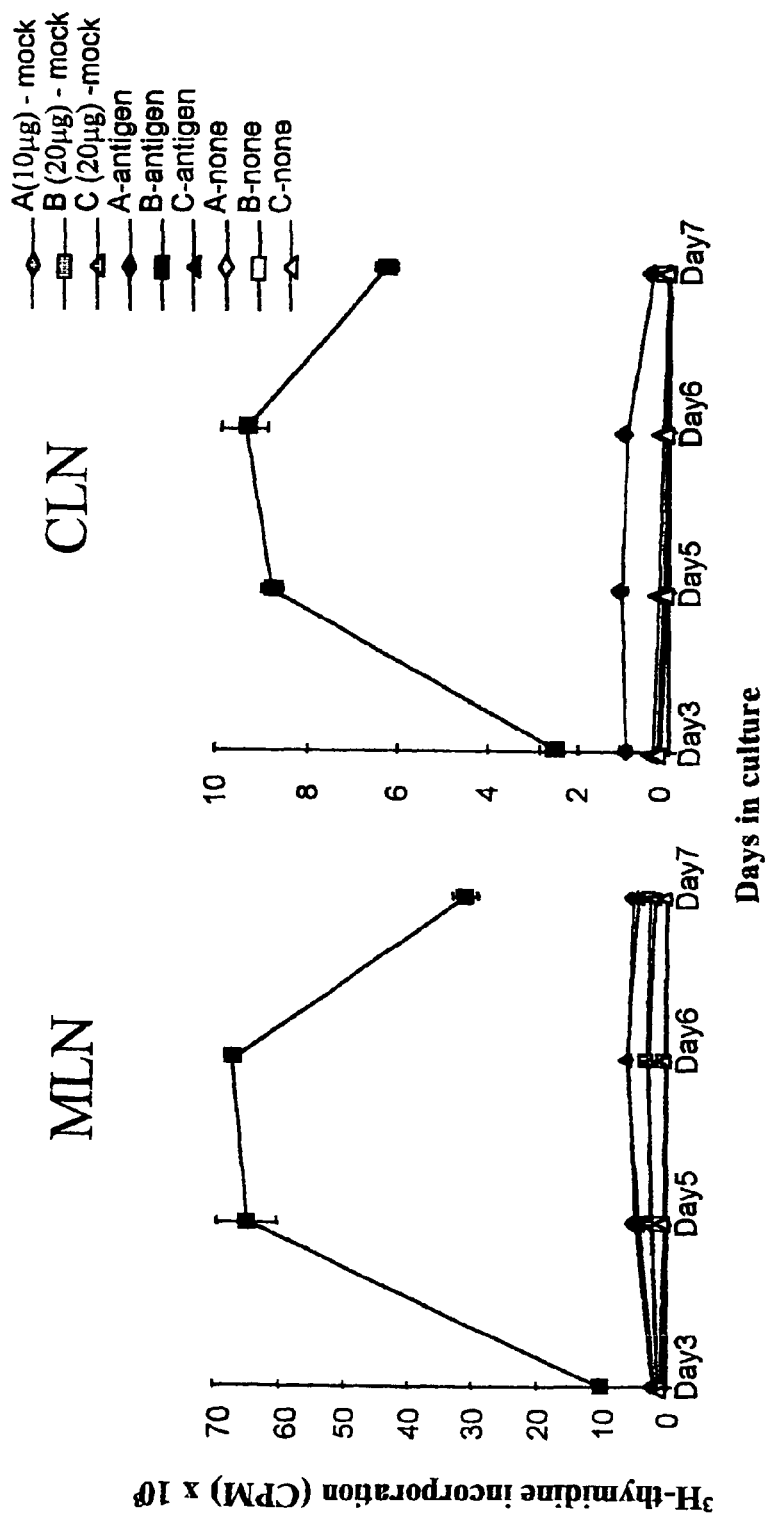

Also, T-lymphocytes from immunised mice from the cervical lymph node (which is local to the vaccination site) and from the mesenteric lymph node (which is distant to the vaccination site) were shown to proliferate when cultured in vitro with HSV-1, but not when cultured in vitro with mock HSV-1 Gp or without antigen (FIG. 2).

Figure 3:
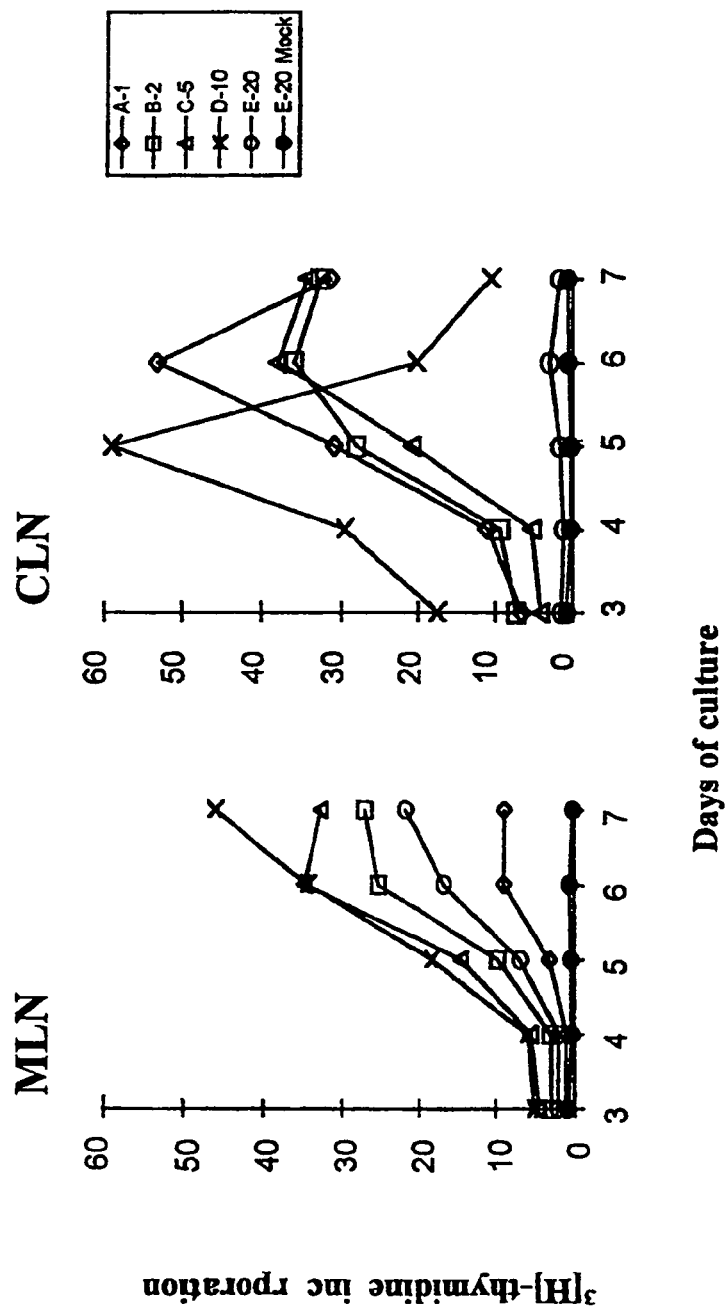

The proliferation in response to HSV-1 Gp of T lymphocytes from mesenteric lymph node (MLN) MLN- and cervical lymph node (CLN) CLN cells of mice immunized with HSV-1 Gp and varying amounts of EtxB is shown in FIG. 3.

The production of Anti-HSV-1 serum Ig in mice following administration of HSV-1 glycoproteins at three day intervals with varying amounts of EtxB (or CtxB) is shown in FIG. 4.

Finally, mice immunised with HSV-1 and rEtxB were shown to have a decrease in virus shedding following corneal scarification with HSV-1 (FIG. 5a), and a decrease in local spreading (oedema and lid disease), spreading to the trigeminal ganglion (zosteriform infection), spreading to the central nervous system (encephalitis) and latency compared to controls (5b).

EXAMPLE 2 rCtxB and rEtxB Act as Immunomodulators

When EtxB is used as an immunomodulator, the Ig isotype distribution is skewed (FIG. 6). The distribution of Ig subclasses is different depending on whether rCtxB or rEtxB is used as an immunomodulator (FIG. 7).

EXAMPLE 3 rEtxB is a More Efficient Immunomodulator than rCtxB

The levels of HSV-specific IgA (FIG. 8) and is greater following stimulation with rEtxB/HSV-1 Gp that rCtxB/HSV-1 Gp.

EXAMPLE 4

FIG. 9

Mice were immunised three times intranasally with HSV-1 glycoproteins alone, a mock preparation of HSV-1 glycoproteins (prepared by taking uninfected tissue culture cells and subjecting them to identical treatment regimes as those employed for the isolation and purification of HSV-1 proteins), or HSV-1 glycoproteins in combination with a variety of putative mucosal adjuvants. In each case the dose of HSV-1 glycoproteins was 10 µg per immunisation, and these were combined with 10 µg of recombinant EtxB, or CtxB as adjuvant, or a mixture of 0.5 µg of Ctx and 10 µg CtxB. Three weeks after the final immunisation, blood samples were collected and total anti-HSV-1 antibodies were measured by ELISA. The quantities of antibodies are expressed as a percentage of the levels stimulated following ocular infection induced by scarification with $10^5$ pfu HSV-1 strain SC16. The data (shown in FIG. 9) shows that the strongest serum antibody response is stimulated when antigen is combined with a mixture of whole Ctx and CtxB. However, a high level response is also stimulated when rEtxB is used as an adjuvant. In contrast, rCtxB is a very weak adjuvant.

EXAMPLE 5

FIG. 10

Mice were immunised as described in example 4. Secretory IgA production in the eye was assessed by taking washings of the tears over consecutive days and these samples were then pooled and subjected to ELISA analysis using a specific anti-IgA detecting antibody. The quantities of antibodies are expressed as a percentage of the levels stimulated following ocular infection induced by scarification with $10^5$ pfu HSV-1 strain SC16. The data clearly demonstrates (FIG. 10) that high levels of secreted anti-HSV-1 antibodies are produced following immunisation in the presence of either Ctx/CtxB or EtxB. In contrast to the results from analysis of serum antibody responses, there was no difference in the level of antibodies in the eye between those animals immunised with Ctx/CtxB or EtxB as adjuvants. As with serum antibody, there was clear evidence that rCtxB is a very poor adjuvant.

EXAMPLE 6

FIG. 11

Mice were immunised as described in example 4. Secretory IgA production in the vagina was assessed by taking washings from the genital tract over consecutive days and these samples were then pooled and subjected to ELISA analysis using a specific anti-IgA detecting antibody. The quantities of antibodies are expressed as endpoint titres which were calculated by linear regression analysis. The data clearly demonstrates that high levels of secreted anti-HSV-1 antibodies are produced in distant mucosal sites following immunisation in the presence of either Ctx/CtxB or EtxB. In the vagina, the highest levels of antibodies were released following immunisation in the presence of rEtxB. Lower levels were released following immunisation with Ctx/CtxB and very little secretion was triggered by the use of rCtxB as adjuvant.

EXAMPLE 7

FIG. 12

Mice were immunised three times intranasally with HSV-1 glycoproteins (10 µg) either alone or in the presence of escalating doses of rEtxB as adjuvant. Three weeks after the final immunisation blood was taken, and the levels of anti-HSV-1 antibodies were assessed by ELISA. The quantities of antibodies are expressed as a percentage of the levels stimulated following ocular infection induced by scarification with $10^5$ pfu HSV-1 strain SC16. The data clearly demonstrates that the capacity of rEtxB to trigger antibody responses to heterologous added antigens is a dose dependent phenomenon with maximal responsiveness occurring at approximately 20-50 µg of rEtxB. Further, it is clear that at doses of 20 µg rEtxB and above, the level of anti-HSV-1 antibodies stimulated by intranasal infection is comparable or greater than that stimulated by a live virulent virus infection.

EXAMPLE 8

FIG. 13

Mice were immunised as described in example 7. Secretory IgA production in the eye was assessed by taking washings of the tears over consecutive days and these samples were then pooled and subjected to ELISA analysis using a specific anti-IgA detecting antibody. The quantities of antibodies are expressed as a percentage of the levels stimulated following ocular infection induced by scarification with $10^5$ pfu HSV-1 strain SC16. The data demonstrates that maximal IgA responses in the eye are stimulated when HSV-1 glycoproteins are given in combination with 20 µg of rEtxB or above. At this dose the levels of IgA production are nevertheless lower than those triggered during virus infection of the eye.

EXAMPLE 9

FIG. 14

Mice were immunised as described in example 7. Secretory IgA production in the vagina was assessed by taking washings from the genital tract over consecutive days and these samples were then pooled and subjected to ELISA analysis using a specific anti-IgA detecting antibody. The quantities of antibodies are expressed as endpoint titres which were calculated by linear regression analysis. The data shows that optimal anti-HSV-1 responses are stimulated in the vagina when 20 μg or above of rEtxB is used as an adjuvant.

EXAMPLE 10

FIG. 15

Mice were either infected with $10^5$ pfu HSV-1 strain SC16 by scarification into the cornea or immunised three times intranasally with 10 μg HSV-1 glycoproteins in combination with Ctx/CtxB or rEtxB. Three weeks after the final inoculation, serum was taken and was analysed by ELISA for the presence of IgG1 and IgG2a against HSV-1. The quantities of antibodies are expressed as endpoint titres which were calculated by linear regression analysis (FIG. 7a). The data clearly shows that the nature of the antibody response to HSV-1 is influenced by the way in which the antigens are presented to the immune system. Infection with HSV-1 predominantly activates Th1 associated antibody production, as characterised by the high levels of the complement fixing antibody isotype, IgG2a. Infection stimulates relatively low levels of the Th2 associated IgG isotype, IgG1. This profile of the immune response is clearly visible when the data is expressed as a ratio of IgG1:IgG2a as shown in FIG. 7b. The ratio is substantially less than 1 following infection. Intranasal immunisation in the presence of Ctx/CtxB as adjuvant triggers the release, predominantly, of Th2 associated IgG1. Significant levels of IgG2a are also produced suggesting that Ctx/CtxB causes activation of Th1 and Th2 cells. The activation of both responses and the relative dominance of Th2 is reflected in the IgG1:IgG2a ratio which is approximately 3. Interestingly the nature of the response to HSV-1 stimulated by rEtxB as adjuvant is almost exclusively Th2 dominated. High levels of IgG1 are produced with only very low amounts of IgG2a. This strong bias toward Th2 responsiveness is reflected in an IgG1:IgG2a ratio of approximately 9.

EXAMPLE 11

FIG. 16

Mice were either infected with $10^5$ pfu HSV-1 strain SC16 by scarification into the cornea or immunised three times intranasally with 10 μg HSV-1 glycoproteins in combination with Ctx/CtxB or rEtxB. Three weeks after the final inoculation lymph nodes were removed from animals and were used to generate single cell suspensions that were cultured either in the presence of killed HSV-1 or a mock preparation of virus from non-infected tissue culture cells. On days 4 to 7 of the cultures, samples of cells were removed and subjected to cELISA analysis to reveal the secretion of cytokines. The data clearly shows that T-cells in the cultures were capable of responding to HSV-1, but not significantly to mock virus preparations. Lymph node cells taken from mice which had been infected with HSV-1 produced predominantly the Th1 associated cytokine γ-interferon (γ-IFN). Lymph node cells taken from animals that were immunised intranasally produced high levels of the Th2 associated cytokines, IL-4 and IL-10. In addition, both Ctx/CtxB and rEtxB had led to the activation of T-cells which secreted γIFN upon in vitro stimulation with HSV-1. This indicates that although the response to these adjuvants is dominated by the production of Th2 cytokines some Th1 activation also occurs. These findings are consistent with those from the analysis of antibody responses.

The invention claimed is:

1. A method of generating a cytotoxic CD8+ T-lymphocyte cell-mediated protective immune response against a herpes virus infection, in a mammal in need thereof, comprising co-administering to the mammal a therapeutically effective amount of *Escherichia coli* heat labile enterotoxin B subunit (EtxB), and an antigen, wherein the EtxB is free from whole toxin and is not linked to the antigen, wherein the antigen is a virus antigen from the herpes virus family, thereby generating the cytotoxic CD8+ T-lymphocyte cell-mediated protective immune response against a herpes virus infection.

2. The method according to claim 1, wherein the virus antigen is an antigen of a virus selected from the group consisting of Herpes Simplex Virus-1 (HSV-1), Herpes Simplex Virus-2 (HSV-2), Epstein-Barr Virus (EBV), Varicella-zoster Virus (VZV), Cytomegalovirus (CMV), Human Herpes Virus-6 (HHV-6), Human Herpes Virus-7 (HHV-7) and Human Herpes Virus-8 (HHV-8).

3. The method according to claim 2, wherein the virus antigen is an antigen of a virus selected from the group consisting of HSV-1, HSV-2, CMV or EBV.

4. The method according to claim 1, wherein the said EtxB and antigen are administered to the said mammalian subject in an amount which is effective to increase the mammalian subject's levels of T cell lymphocyte response to the antigen.

5. The method of claim 1, wherein the EtxB and antigen are administered to the mammal in need thereof in multiple doses.

6. A method of generating a cytotoxic CD8+ T-lymphocyte cell-mediated protective immune response against an infection, in a mammal in need thereof, comprising administering to the mammal between 50 and 100 ug of *Escherichia coli* heat labile enterotoxin B subunit (EtxB), wherein the EtxB is free from whole toxin, and an antigen, wherein the EtxB and antigen are not linked to form a single active agent.

7. The method of claim 6, wherein the EtxB and antigen are administered to the mammal in need thereof in multiple doses.

* * * * *